United States Patent
Giessler-Blank et al.

(10) Patent No.: US 9,351,485 B2
(45) Date of Patent: May 31, 2016

(54) USE OF SOPHOROLIPIDS AND DERIVATIVES THEREOF IN COMBINATION WITH PESTICIDES AS ADJUVANT/ADDITIVE FOR PLANT PROTECTION AND THE INDUSTRIAL NON-CROP FIELD

(75) Inventors: Sabine Giessler-Blank, Dortmund (DE); Martin Schilling, Bonn (DE); Oliver Thum, Ratingen (DE); Ewald Sieverding, St. Johann (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 13/497,588

(22) PCT Filed: Aug. 30, 2010

(86) PCT No.: PCT/EP2010/062600
§ 371 (c)(1),
(2), (4) Date: Mar. 22, 2012

(87) PCT Pub. No.: WO2011/039014
PCT Pub. Date: Apr. 7, 2011

(65) Prior Publication Data
US 2012/0220464 A1 Aug. 30, 2012

(30) Foreign Application Priority Data
Sep. 29, 2009 (DE) .......................... 10 2009 045 077

(51) Int. Cl.
| | | |
|---|---|---|
| *A01P 13/00* | (2006.01) | |
| *A01N 43/16* | (2006.01) | |
| *A01N 25/00* | (2006.01) | |
| *A01N 43/647* | (2006.01) | |
| *A01P 21/00* | (2006.01) | |
| *A01N 47/34* | (2006.01) | |
| *C07H 19/01* | (2006.01) | |
| *A01P 7/04* | (2006.01) | |
| *A01P 3/00* | (2006.01) | |
| *A01N 25/30* | (2006.01) | |

(52) U.S. Cl.
CPC ................ *A01N 25/30* (2013.01); *A01N 43/16* (2013.01)

(58) Field of Classification Search
CPC ............................... A01N 25/30; A01N 43/16
See application file for complete search history.

(56) References Cited

U.S. PATENT DOCUMENTS

| | | | |
|---|---|---|---|
| 4,215,213 A | 7/1980 | Inoue et al. | |
| 4,216,311 A | 8/1980 | Inoue et al. | |
| 5,326,407 A | 7/1994 | Baviere et al. | |
| 6,184,182 B1 * | 2/2001 | Gillespie et al. | 504/206 |
| 2005/0164955 A1 | 7/2005 | Gross et al. | |
| 2007/0191292 A1 | 8/2007 | Gandhi et al. | |
| 2007/0207930 A1 * | 9/2007 | Gandhi et al. | 504/358 |

FOREIGN PATENT DOCUMENTS

| | | |
|---|---|---|
| DE | 29 052 52 A1 | 8/1979 |
| DE | 29 052 95 A1 | 8/1979 |
| JP | 54-109913 | 8/1979 |
| JP | 54-109914 | 8/1979 |
| JP | 2008-501039 | 1/2008 |
| KR | 2002-0003679 | 1/2002 |
| WO | 98/16192 A1 | 4/1998 |
| WO | 2005/117929 A1 | 12/2005 |
| WO | WO 2006/096912 A1 | 9/2006 |

OTHER PUBLICATIONS

Hu et al., "Purification of lactonic sophorolipids by crystallization", Journal of Biotechnology, (2001), vol. 87, Issue 3, pp. 263-272.*
Hirata et al., "Novel characteristics of sophorolipids, yeast glycolipid biosurfactants, as biodegradable low-foaming surfactants" Journal of Bioscience and Bioengineering (Aug. 2009) vol. 108, No. 2, pp. 142-146.*
Nitschke et al., "Biosurfactants in food industry" Trends in Food Science & Technology (2007), vol. 18, pp. 252-259.*
Felse, P. A., et al., "Sophorolipid biosynthesis by Candida bombicola from industrial fatty acid residues", Enzyme and microbial technology, Jan. 2007, 40, pp. 316-323.
Muthusamy, K., et al., "Biosurfactants: Properties, commercial production and application", Current Science, Mar. 2008, vol. 94, No. 6.
Kosaric N., "Biosurfactants and Their Application for Soil Bioremediation", Food Technol. Biotechnol. 39(4):295-304 (2001).
Notice of Reasons for Rejection dated Jul. 30, 2014 received from the Japanese Patent Office from related Application No. 2012-530202, together with an English-language translation.
Ratsep P. et al., "Identification and Quantification of Sophorolipid Analogs Using Ultra-Fast Liquid Chromatography-Mass Spectrometry", Journal of Microbiological Methods 78:354-356 (2009).
Australian Examination Report dated Jul. 11, 2014 received from related Application No. 2010300168.
European Office Action dated Jul. 9, 2013 received from related Application No. 10 749 837.0.
Van Bogaert, Inge N.A., "Microbial production and application of sophorolipids", Applied Microbiology and Biotechnology (May 3, 2007), vol. 76, No. 1, pp. 23-24.
Nitschke, M., et al., "Biosurfactants in food industry", Trends in Food Science & Technology (Apr. 29, 2007), vol. 18, No. 5, pp. 252-259.
Davila, A.M. et al., "Sophorose lipid fermentation with differentiated substrate supply for growth and production phases", Applied Microbiology and Biotechnology (May 1, 1997), vol. 47, No. 5, pp. 496-501.

(Continued)

*Primary Examiner* — Abigail Fisher
*Assistant Examiner* — Daniel Branson
(74) *Attorney, Agent, or Firm* — Scully, Scott, Murphy & Presser, P.C.

(57) ABSTRACT

Use of sophorolipids as adjuvants in combination with pesticides as tank mix additive and/or as formulation additive for crop protection and for the industrial non-crop sector.

14 Claims, No Drawings

(56) References Cited

OTHER PUBLICATIONS

Jeneil Biosurfactant Co., LLC, "JBR425 Product Data Sheet" (Aug. 16, 2001), pp. 1-5, Retrieved from the Internet: URL:http://web.archive.org/web/20050308124017/biosurfactant.com/downloads/jbr425pds.pdf (retrieved on Dec. 7, 2010).

Environmental Protection Agency, "Rhamnolipid Biosurfactant: Exemption from the Requirement of a Tolerance", Federal Register (Mar. 31, 2004), vol. 69, No. 62, pp. 16796-16800.

International Search Report dated Dec. 27, 2010 issued in PCT/EP2010/062600.

Blackburn, G. M., et al., "Strain Effects in Acyl Transfer Reactions. Part III., Hydroxide and Buffer-catalysed Hydrolysis of Small and Medium Ring Lactones", J. Chem. Soc., Perkin Trans. 2, 1974, 377-382.

Huisgen, R., et al., "Die Konfiguration Der Carbonestergruppe Und Die Sondereigenschaften Der Lactone", Tetrahedron, 1959, pp. 253-267, vol. 6, Pergamon Press Ltd., Printed in Northern Ireland, with English-language abstract.

\* cited by examiner

USE OF SOPHOROLIPIDS AND DERIVATIVES THEREOF IN COMBINATION WITH PESTICIDES AS ADJUVANT/ADDITIVE FOR PLANT PROTECTION AND THE INDUSTRIAL NON-CROP FIELD

The invention relates to the use of sophorolipids and/or derivatives thereof and compositions as a formulating additive and/or tank mix additive (also called adjuvant) for pesticides or pesticide mixtures.

In crop protection, in pest control compositions and also in the industrial non-crop sector, the purpose of improving the biological activity of such pesticides or pesticide mixtures is often pursued by using what are called adjuvants or else auxiliaries or added substances. The activity is frequently also referred to as efficacy. The Pesticides Safety Directorate (PSD, the executive arm of the Health and Safety Executive, a non-state, public organization in Great Britain) defines an adjuvant as a substance other than water which is not in itself active as a pesticide but which enhances or supports the effectiveness of a pesticide (http://www.pesticides.gov.uk/approvals). These substances are either added to the aqueous spray solutions shortly before delivery and spray application (as a tank mix additive) or incorporated directly into crop protection product formulations. In the context of the use of the word "adjuvant", patents or the literature often use, as synonym, the terms "surfactant" or "wetting agent", which, however, are far too wide-ranging and may be interpreted more as a generic term. On the basis of the use advised here, recourse is made to the term "adjuvant", since this better describes the function of the sophorolipids. Sophorolipids, as will be shown later, produce virtually no wetting/spreading. In contrast, many of the surfactants or wetting agents known in crop protection display a very high spreading behavior, including, for example, trisiloxanes.

In the art there are numerous crop protection active ingredients which achieve acceptable efficacy, i.e., an effect with practical relevance, only with the aid of adjuvants. The adjuvants help here to compensate the weaknesses of the active ingredient, such as, for example, the UV sensitivity of avermectins (which are degraded by ultraviolet radiation) or the water instability of sulfonylureas. More recent active ingredients are generally not water-soluble, and, in order to be able to distribute them effectively on a target=target organism=plants, adjuvants are vital in the aqueous spray solution, in order to compensate the poor wetting of surfaces, by means of the physical influencing of the aqueous solutions. Moreover, adjuvants help to overcome technical application problems, such as low water application volumes, varying water qualities, and the trend of increased application speeds. Enhancing the pesticide activity and compensating weaknesses of the crop protection products by means of adjuvants is generally referred to as boosting the efficacy of the application of crop protection products.

The unskilled person might suppose that all commercially available wetting agents/surfactants (in the cosmetics segment or in the household cleaning products sector, for example) boost the efficacy of pesticides. That, however, is not the case, as has also been observed in numerous publications (see, for example, in Pesticide Formulation and Adjuvant Technology, edited by Chester L. Foy and David W. Pritchard. CRC Press LLC, 1996, pages 323-349).

It is, therefore, surprising and nonobvious that sophorolipids boost the efficacy of pesticides, and therefore behave as adjuvants.

Certain publications teach that certain glycolipids, such as rhamnolipids, may themselves exert an intrinsic pesticidal effect (US 2005/0266036 or else Yoo D S, Lee B S, Kim E K (2005), Characteristics of microbial biosurfactant as an antifungal agent against plant pathogenic fungus. J Microbiol Biotechnol 15:1164-1169). It should therefore be stated that this patent application does not describe adjuvants within the meaning of the definition of the UK PSD.

US 2005/0266036 A1 describes biological wetting agents, produced by microbes, for use against pests, as for example of nematodes. Here, the wetting agents or the microorganisms which produce the wetting agents are placed directly, as biopesticides, so to speak, onto the pests, for direct control thereof. Examples are given only for the use of rhamnolipids against house flies, cockroaches, and nematodes, and also against existing fungal spores on squash. The use concentration of the biological wetting agent, in this case a rhamnolipid, was very high in the case of herbicides, at 5% by weight in the spray solution. Even crop protection active ingredients are not used at such a high application concentration. Usually (although there are other application concentrations) about 1 l/ha of crop protection formulation (containing not more than 500 g/l of active ingredient) is used with a water quantity of about 250 l/ha. This corresponds to a maximum concentration of about 0.4% by weight. Information on the controlled and/or selective control of pests with practically-relevant activity, and also on the preventive effect, in other words protective effect, however, is not given in the US patent application cited above.

"Protective" means that the pesticide/adjuvant combination is applied to the target organism when the disease or the pest organism has not yet appeared (i.e., protective delivery before the appearance of pests or diseases). Protective applications are important for fungicides especially, but also for insecticides and acaricides.

US 2005/0266036 A1 does not reveal whether rhamnolipids also boost the efficacy of herbicides if they are used at a selective dose (i.e., as an adjuvant). Selective doses are those at which the glycolipid itself produces no control (damage) of the pest organism (such as weed, insect, fungus or suchlike pest organism).

The application US2005/0266036 describes how the biosurfactants used therein, especially rhamnolipids, display a pesticidal activity on account of their cell wall penetration effect. Penetration promoters of this kind are in fact often necessary for crop protection products, in order to control a pest organism which is already present within the plant tissue, this being referred to as curative effect. The patent application cited above, however, does not indicate in any way, and nor is it evident, that glycolipids, if they were to be combined with crop protection products, would also act protectively or even substantially improve the efficacy of said products. In the crop protection sector, contact agents such as the fungicide sulfur, for example, are usually used for protective defense. These active ingredients, however, act only via contact—in other words, the pests must be struck. For curative protection, in contrast, active ingredients with a systemic effect are usually used, such as, for example, rimsulfuron (from the group of the sulfonylureas) or epoxiconazole (from the group of the triazole fungicides). This kind of active ingredients is taken up by the plant and transported in the plant sap. Pests feed on or suck from plants, and so consume the product.

Synergism here is understood to mean that the effect of the combination of pesticide and adjuvant is greater than the anticipated effect of the two individual components (see Colby formula: Colby S. R. 1967. Calculating synergistic and antagonistic responses of herbicide combinations. Weeds 15:20-22). Of such a synergistic effect in the interaction of pesticide and sophorolipids there is no evidence to be found in the prior art.

In crop protection, in pest control and in the industrial sector, chemical or biological crop protection products (also called pesticides below) or pesticide mixtures are employed. These may be, for example, herbicides, fungicides, insecticides, growth regulators, molluscicides, bactericides, viricides, micronutrients, and also biological crop protection agents based on natural substances or living or processed or engineered microorganisms. Active pesticidal ingredients are listed in conjunction with their areas of use, for example, in 'The Pesticide Manual', 14$^{th}$ edition, 2006, The British Crop Protection Council; active biological ingredients are given, for example, in 'The Manual of Biocontrol Agents', 2001, The British Crop Protection Council. Pesticide below is always used as a collective term. As tank mix additives it is common to use alkoxylated trisiloxane surfactants, which lower the static surface tension of spray solution or water to a significantly greater degree than do organic surfactants used in the past, such as nonylphenol ethoxylates, for example. Trisiloxane surfactants have the general structure $Me_3SiO$—$SiMeR$—$OSiMe_3$, where the radical R represents a polyether radical. The use of superspreading trisiloxane surfactants, such as BREAK-THRU® S-240, Evonik Goldschmidt GmbH, for example, in combination with a pesticide leads to an improvement in the uptake of pesticide by the plant and, generally, to an increase in its activity or its efficacy. U.S. Pat. No. 6,734,141 describes how for this efficacy boost it is specifically a low surface tension and not necessarily the spreading that is responsible. In the majority of patents, the term "surface tension" always refers to the static surface tension. In the case of trisiloxanes, for example, the static surface tension is about 20 to 25 mN/m.

In numerous countries, however, trisiloxane surfactants are classed as harmful to health, and in the context of registration as an ingredient of crop protection products this is considered to be a criterion for exclusion. Numerous tank mix additives, especially ethoxylated alcohols or alkylpolyglycosides, cause severe foaming in spray solution on stirred incorporation, and this foaming may possibly lead to problems in the field on application. Generally, synthetic wetting agents must, in order to obtain registration as adjuvants before the national authorities, be shown not to give rise to any residues in the soil. This residue problem, which in the majority of countries exists only for active pesticidal ingredients, is being applied more and more to traditional adjuvants as well. Biological wetting agents, being biodegradable, would not be affected by this problem, and this represents a strong advantage for this application. Glycolipids are understood to be a class of chemical compounds which are composed of a hydrophilic carbohydrate moiety and a hydrophobic lipid moiety and which on account of their amphiphilic nature have interface-active or surfactant properties and are therefore also referred to as biosurfactants. Oftentimes they are hydroxylated fatty acids which are linked by a glycosidic bond to a sugar residue. This class of compound also includes products of microbial metabolism. Examples of such are rhamnolipids (RL), sophorolipids (SL) and mannosylerythritol lipids (MEL), synthesized respectively by bacteria (e.g., *Pseudomonas aeruginosa*), yeasts (e.g., *Candida bombicola*), or yeasts and higher fungi (e.g., *Candida antarctica* and *Pseudozyma aphidis*).

The biotechnology synthesis of such compounds has been known for some considerable time already, and suitable strains and fermentation conditions have undergone in-depth investigation (e.g., Mukherjee, S. et al.—2006, Towards commercial production of biosurfactants, Trends in Biotechnology, Vol. 24, No. 11). In recent times, however, there has been a sharp increase in interest in this class of compound, as part of the sustainability debate, since they can be produced under gentle conditions from renewable raw materials.

For this purpose, in principle, the microorganism in question is supplied with a metabolizable carbohydrate (e.g., a monosaccharide or a disaccharide) as hydrophilic substrate, and, as hydrophobic substrate, a hydrocarbon, fatty alcohol, a fatty acid, a triglyceride or corresponding mixtures, which are converted by said microorganism into the corresponding target compound. In this context, the origin of the two substrates may vary greatly, since required elements of the target molecule can if necessary also be synthesized through the metabolism of the microorganism, thereby opening access to a very broad spectrum of carbohydrate or hydrocarbon sources (K. Muthusamy et al.—2008, Properties, commercial production and applications, Current Science, Vol. 94, No. 6, pp. 736-747). Examples of possible hydrophobic substrates are longer-chain hydrocarbons, plant or animal oils, free fatty acids or fatty acid derivatives (cf. EP 1 953 237 A1, esters of different chain lengths, etc.), and also fatty alcohols. The hydrophilic carbon source usually used is glucose, though depending on the organism employed other sugars as well, such as lactose and sucrose, for example, are also accepted (van Bogaert et al.—2006, Microbial production and application of sophorolipids, Applied Microbiology and Biotechnology, Vol. 76).

Another possibility for structural diversification and associated expansion of the functional properties is the subsequent chemical or biochemical modification of the microbially generated glycolipids. For this as well, various methods have been described, as for example in US 2007/027106-A1—Charged Sophorolipids and sophorolipid containing compounds, or in US 2005/164955A1—Antifungal properties of various forms of sophorolipids, or in Bisht, K. S. et al.—1999, Enzyme-mediated regioselective acylation of SLs, The journal of organic chemistry, 64, pp. 780-789; Azim, A. et al.—2006, Amino acid conjugated sophorolipids, Bioconjugate Chemistry, 17, pp. 1523-1529). One simple method, for example, is the base-catalyzed hydrolysis or esterification with aliphatic alcohols of various chain lengths. One interesting method of preparing sophorolipids having short hydrophobic radicals was recently published likewise in EP 1 953 237 A1. The hydrophobic substrate supplied as feed in this case comprises fatty acid analogs which contain, for example, amide bonds, ester bonds or double bonds and can be subsequently cleaved chemically, by hydrolysis or ozonolysis, in order to obtain shorter-chain hydrophobic radicals.

Reducing the water content in crude sophorolipid products, by distillation, for example, leads to technical problems during processing, since the products become very high in viscosity. This problem has been solved by the addition of volatile polyols which are viscosity-reducing even at low concentration; see U.S. Pat. No. 4,197,166—Dehydrating purification process for a fermentation product.

Within the technical literature, glycolipids, in the form of the representatives rhamnolipids, trehalose lipids, and sophorolipids, have been disclosed as biological surfactants (Desai J D and Banat I M. Microbial Production of Surfactants and their Commercial Potential. Microbiology and Molecular Biology Reviews, March 1997, pp. 47-64). They are used, for example, for soil remediation (see Master Thesis Özlem Zenginyürrek, Izmir 2002, Izmir Institute of Technology: Title: Effects of biosurfactants on remediation of soils contaminated with pesticides; or Food Technology and Biotechnology (2001), 39 (4), 295-304). These publications also describe the breakdown of pesticides, such as of endosulfan or metalachlor, in soils. In these cases, the biological wetting agents are applied directly to the soil. In the literature and also in patents, rhamnolipids are mostly associated with biological wetting agents. These rhamnolipids, however, are labeled as hazardous to health, and according to safety data sheets can cause serious eye damage.

The trend within the agro sector is increasingly toward less toxicologically objectionable additives and adjuvants. Moreover, the preparation of rhamnolipids is hindered by severe foam formation in the course of their fermentative production, and efficient biotechnological production has to date been realizable only with potentially pathogenic strains of the genus *Pseudomonas*. In the context of this invention, therefore, rhamnolipids have not been pursued any further. MEL (Mannosyl Erythritol Lipids) are further lipids which would be contemplated as adjuvants. Since, however, they are very hydrophobic in terms of the molecule, and can therefore be dispersed only with difficulty, if at all, in water, their applicability would be limited to oil-based formulations, since a prerequisite for use as a tank mix additive is that molecules are water-soluble. MELs could therefore be used preferably only in combination with co-surfactants. PCT/US2005/046426 (WO2006/069175) describes sophorolipids for use as antifungal agents, but not in connection with crop protection or non-crop applications. The antifungal agent quality is utilized in the cosmetics segment and in medicine (K. Kim et al.—Journal of Microbiology and Biotechnology (2002), 12(2), 235-241). In the cosmetics segment, biological wetting agents are usually used as emulsifiers for oil-in-water emulsions (I. van Bogaert et al.; Appl. Microbiol Biotechnology (2007) 76: pp. 23-34). van Bogaert et al. also report on the commercial use of biological wetting agents, especially sophorolipids, in household cleaning products.

Crop protection product formulations, which for use are usually diluted with water prior to the customary delivery by spraying via nozzles, comprise not only the active pesticidal component or treatment component (called active substance or else active ingredient) but also other auxiliary agents, such as emulsifiers, thickeners, dispersing aids, antifreeze agents, defoamers, biocides and/or surface-active substances, for example; the skilled formulator is familiar with such substances.

The type of formulation is influenced by the crop plant, the area of cultivation, and the user. On account of the diversity of physicochemical properties among the different active pesticidal ingredients, there exists on the market a large number of both liquid and solid formulation types. The formulation additives, especially the adjuvant, give rise to particular application properties such as retention, penetration, rain resistance, and spreading behavior. A specific formulation is intended to ensure that the smallest possible amount of active ingredient can be distributed uniformly over a large area (reducing the application rates to protect the consumer and the environment), but while continuing to ensure maximum performance and activity. Widespread types of formulation, listed only by way of example here, are as follows: suspension concentrates, capsule suspensions, emulsifiable concentrates, water-soluble concentrates, oil dispersions, suspoemulsions, emulsions in water, water-dispersible granules or powders. The possible types and varieties of formulation are not to be limited to those described here.

Active ingredients of these kinds are often added to a tank containing water in order to dilute the concentrated formulation of the active ingredient prior to spray delivery, and to make it compatible with the plants. Tank mix additives (also called added substances or adjuvants) are added to the water in the same tank separately before or after the active ingredient formulation, and are distributed by stirring with the entire system referred to as the spray solution.

Active ingredients (active substances) are substances which within the individual countries are approved and/or registered for application to plants and crops, and/or are listed for protecting plants from damage, or in order to avoid loss of yield in a crop or to reduce such loss. Such active ingredients or substances may be synthetic or else biological in type. Such active ingredients may also be extracts or natural substances, or organisms with an antagonistic action. They are commonly also referred to as pesticides. In the present invention here, the nature of the active ingredient is not important, since the tank mix additive utility is of general nature and is not specific to the active ingredient. The pesticides, which are named in crop protection according to their area of application, include, for example, the following classes: acaricides (AC), algicides (AL), attractants (AT), repellents (RE), bactericides (BA), fungicides (FU), herbicides (HE), insecticides (IN), molluscicides (MO), nematicides (NE), rodenticides (RO), sterilizers (ST), viricides (VI), growth regulators (PG), plant strengtheners (PS), micronutrients (MI), and macronutrients (MA). These designations and the areas of application are familiar to the skilled person. Active ingredients are used alone or in combinations with other active ingredients. Preferred pesticides are HB, FU, IN, PG, MI, and particularly HB, FU, IN. In commerce, such active ingredients or substances are mostly sold generally in formulated form, since only in such a form can they be used by the user and, following their dilution, usually with water, can be delivered.

Some active ingredients or active organisms are listed by way of example in 'The Pesticide Manual', $14^{th}$ edition, 2006, The British Crop Protection Council, or in 'The Manual of Biocontrol Agents', 2004, The British Crop Protection Council. The present specification, however, is confined not only to these active ingredients listed there, but also includes more modern active ingredients not yet cited in the aforementioned monograph. No listing will be given here of the individual active ingredients or of formulations of these active ingredients, or of active ingredient combinations with one another or between one another.

Products with natural substance character, or biological products, are also listed in one of the publications cited above. Plant nutrients and plant micronutrients, which are delivered in liquid form in a liquid preparation in any of the wide variety of forms, alone or in combination with other nutrients, or in combination with crop protection products, include, for example, nitrogen, phosphate, potassium, calcium, magnesium, manganese, boron, copper, iron, selenium, cobalt, and others, which are referred to as micronutrients.

There is a need for biological substances which are toxicologically unobjectionable, are not environmentally hazardous according to EC Directive 1907/2006, greatly lower the surface tension of water, are water-soluble or dispersible, and can be used as a tank mix additive and also as a formulating auxiliary in order to promote selective activity in pesticides. Toxicologically unobjectionable in the context of this invention means that the desired biological substances are, for example, biodegradable, have no negative (i.e., >10 mg/l) toxicity for fish, daphnia and/or algae, and do not cause eye irritation to the user. Preferred use concentrations in the tank mix sector lie between 0.001-3% by volume, preferably 0.01-0.5% by volume, and more preferably below 0.1% by volume (corresponding also to about 0.1% by weight) of the spray solution. This is synonymous with 10-3000 ml/ha, when typically 100 to 1000 l of spray solution per hectare are delivered, and preferably an adjuvant amount of 50-700 ml/ha, which are also added by the respective spray solution quantities independently of the total water application rate per hectare. As a formulating auxiliary, this concentration must be calculated back to the crop protection product concentrate and its application rate.

The aforementioned quantity of adjuvant corresponds to the use concentration on the field.

It is an object of the present specification, therefore, to find toxicologically unobjectionable adjuvants which boost the efficacy of pesticides.

The object is achieved through the use of adjuvants/additives based on sophorolipids.

The present invention accordingly provides for the use of adjuvants comprising sophorolipids, sophorolipid preparations, and derivatives thereof, as a tank mix additive themselves, or as a formulating additive, as an emulsifier, dispersant, defoamer, or generally, as a wetting agent, in each case with the function of the adjuvant, for crop protection and/or for the industrial non-crop sector. As derivatives it is possible with preference to use sophorolipid esters.

The adjuvants of the invention comprising sophorolipids preferably boost the action of pesticides and/or enhance the activity, preferably by more than 10% relative to use without the sophorolipids and their preparations or derivatives, with the proviso that the dose range of the adjuvant lies between 10-3000 ml/ha, preferably between 30-1000 ml/ha, and more preferably between 50-700 ml/ha.

Preference is given to using pesticides and/or fungicides in the sense of crop protection products and industrial pest-control compositions, selected for example from the group of the herbicides, insecticides and/or growth regulators or mixtures thereof or plant strengtheners, micronutrients and macronutrients, especially when the combinations of pesticide and adjuvant are employed protectively. Particular preference here is given to the use of the sophorolipids in pesticide applications as a tank mix additive or formulating auxiliary. In these cases the adjuvants ought to cause little foaming and hence to develop less than 80 ml of foam after 30 seconds in accordance with CIPAC Method MT 47, and/or to induce no eye irritation for the user, and/or to lower the surface tension of water to levels of less than 40 mN/m, based on a 0.1% strength by weight aqueous solution of the adjuvant.

A synergistic effect of the adjuvant together with the pesticide is preferred. The efficacy of the pesticidal activity of these preferred compositions of the invention is higher than the efficacy of the pesticide or of the adjuvant alone, or their additive effect, and in one preferred embodiment the adjuvant alone has no pesticidal activity itself in the use concentration range. This synergistic effect occurs preferably in a concentration range and in a ratio of active pesticidal ingredient to adjuvant of 1:120 to 30:1, preferably 1:100 to 20:1, very preferably 1:75 to 4:1. This concentration range relates to the use as tank mix additive and as formulating additive.

As pesticides it is preferred to use herbicides and/or fungicides and mixtures thereof. Particularly preferred are herbicides or fungicides, more preferably contact fungicides such as sulfur, for example, and/or else systemic fungicides from the class of the triazoles, and/or systemic herbicides from the group of the sulfonylureas, and also mixtures of these and other pesticides.

In one preferred embodiment the adjuvants/additives can be used together with other co-surfactants, examples being carboxylic acids. Carboxylic acids used are preferably alkanoic acids having a straight, saturated alkyl chain of 6 to 10 carbon atoms, or preferably octanoic acid (caprylic acid), nonanoic acid, decanoic acid (capric acid), oleic acid or mixtures thereof.

The adjuvants can be used as additives in pesticide formulations, such as, for example, suspension concentrates, capsule suspensions, emulsifiable concentrates, water-soluble concentrates, oil dispersions, suspoemulsions, emulsions in water, water-dispersible granules or powders, alongside other added substances, such as, for example, dispersants, emulsifiers, thickeners, and defoamers, with an adjuvant content of 1% by weight to 99% by weight, preferably in the range from 1.5% by weight to 60% by weight, and more preferably from 1.9% to 30% by weight.

Additionally provided by the invention are compositions which comprise sophorolipids and at least one active pesticidal ingredient, and in one preferred embodiment the sophorolipid itself exerts no inherent pesticidal effect.

The invention additionally provides compositions comprising sophorolipids and active pesticidal ingredients, the pesticidal efficacy and activity of the composition being greater than the sum of the efficacies of the individual components. The efficacy here is relative both to the total amount and to the relative ratios. An optimum efficacy is obtained at a ratio of active pesticidal ingredient to adjuvant of 1:100 to 20:1, preferably 1:75 to 4:1.

The compositions that are provided by the invention comprise sophorolipids, which can be prepared by fermentative processes. Owing to the heterogeneous composition of the reactants (e.g., mixtures of fatty acids), and the restricted selectivity of the microbial biosynthesis apparatus, the substances are present not as pure compounds but instead as natural mixtures.

The sophorolipids, according to the provisions of this invention, are therefore understood to include sophorolipid preparations and compositions which following fermentative preparation can be used without further purification and employed.

The sophorolipids according to this definition, and the sophorolipid preparations, may therefore comprise, for example, reactants from the fermentation process, such as fatty acids and carbohydrates, for example, which have served as substrates for the microorganisms, and also, for example, water and other natural impurities, especially organic impurities. Certain sophorolipid forms are not pH-stable. Under base catalysis, for example, therefore, there may be a deacetylation or a lactone opening, with formation of the analogous acid form.

One preferred embodiment of the invention uses sophorolipids and derivatives thereof, and also sophorolipid preparations, as a constituent of adjuvants/additives in crop protection and/or in the non-crop sector.

Based on solids, the sophorolipids are present in a purity of >30% by weight, preferably >65% by weight (m/m), more preferably >80% by weight (m/m). The adjuvants may comprise to an extent of 1% to 100% by weight the sophorolipids themselves, their derivatives, or sophorolipid preparations. The amount of the sophorolipids, derivatives thereof or the sophorolipid preparations in the adjuvant, based on solids, is preferably greater than 30% by weight, and more particularly greater than 60% by weight.

As the hydrophobic substrate in the fermentative preparation it is possible to use hydrocarbons, fatty acids, fatty acid esters and/or fatty alcohols, preference being given to the use of triglycerides such as, for example, tallow, sunflower oil, rapeseed oil, safflower oil, soyabean oil, palm oil, palm kernel oil, coconut oil, and olive oil, or mixtures thereof, besides the hydrophilic substrate.

The sophorolipid fraction in the adjuvant may, in purified or unpurified form, alternatively:

i) be present as a mixture of lactone and acid form, with an acid fraction of 10% to 100% by weight, preferably <60% by weight, more preferably <20% by weight, or ii) consist to a fraction of >90% by weight of the lactone form, which can be solubilized by adjustment of the pH to a level between 6 and 8, or iii) be present as methyl ester or ethyl ester, with a fraction of 1% to 100% by weight, preferably >50% by weight, and more particularly >90% by weight (m/m) of the respective ester.

Surprisingly it has been found that the lactone form of the sophorolipids can also be solubilized at a pH of 6-8 by fatty acids still present from the fermentation or by fatty acids added additionally.

It is particularly surprising that in this case clear systems were obtained, since at a pH of 6 neither the lactone form of the sophorolipid nor the fatty acid on their own are "soluble" with clarity. Only the combination of lactone form and fatty acid is "soluble" with clarity. "Soluble" with clarity here means that an at least apparent true solution is obtained, which may also be present, however, in the form of a fine emulsion. The characteristic feature at any rate is that the emulsion that may be present does not break down into individual phases again.

The invention accordingly further provides a process for preparing a solubilized lactone form of the sophorolipids by bringing the lactone form into solution through the presence of fatty acids, by adjustment of the pH to 6-8, and also provides the solutions or emulsions prepared in this way. The pH may be adjusted by adding inorganic alkalis such as sodium hydroxide solution, for example, or by further addition of fatty acid, depending on whether the pH is to be raised or else lowered.

Suitable fatty acids include the fatty acids that have not undergone complete reaction during the fermentation, and/or may be added additionally. The fatty acids correspond to the acid components of the triglycerides used as substrates, selected from the group consisting of tallow, sunflower oil, rapeseed oil, safflower oil, soyabean oil, palm oil, palm kernel oil, coconut oil, and olive oil, or else short-chain to medium-chain carboxylic acids having an alkyl chain length of 6 to 22 carbon atoms. Preferred examples of fatty acids already present or else added are nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), octadecaenoic acid (oleic acid) or mixtures thereof.

In one preferred embodiment the sophorolipid-containing adjuvant in a 0.1% by weight aqueous solution has a surface tension of <40 mN/m.

Besides the sophorolipid and any organic and inorganic solvents, preferably water, the adjuvant may comprise further added substances known to the skilled person.

The sophorolipids may also be admixed with organic acids or oils, preferably those specified above, and the mixtures obtained can then be used as mixture constituents of tank mix additives.

The invention further provides for the use of sophorolipids in crop protection product formulations, in each case with the function as emulsifier, dispersant, defoamer or, generally, as wetting agent.

One particularly preferred embodiment of the present invention uses sophorolipid preparations which comprise sophorolipids of the formula 1 or 1a,

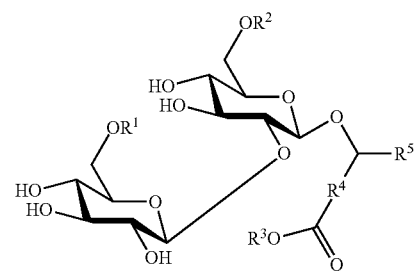

Formula 1

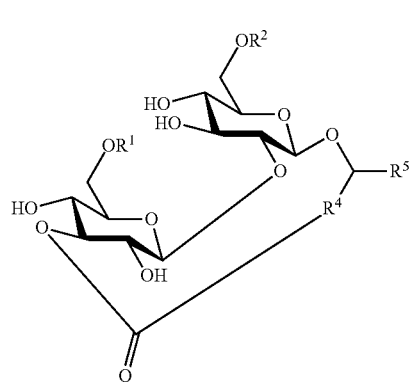

Formula 1a where $R^1$ and $R^2$ independently of one another are either H or an acetyl group, $R^3$ is H or a methyl, ethyl or hexyl group, $R^4$ independently at each occurrence is a saturated or unsaturated divalent, branched or unbranched organic group, preferably a hydrocarbon group having 1-28 carbon atoms which may optionally be interrupted by amine, ester, amide or thioester groups and also is preferably at least monounsaturated, $R^5$ is H or a methyl group, with the proviso that the total number of carbon atoms in the groups $R^4$ and $R^5$ does not exceed the number 29 and preferably is 12 to 20 and more particularly is 14 to 16.

The organic group $R^4$ may be a carbon chain which may optionally be interrupted by heteroatoms such as N, S, and O and hence may also be interrupted by amine, ether, ester, amide or thioester groups.

Additional subject matter provided by the invention is described by the claims, whose disclosure content in its full extent is part of this description.

In the examples set out below, the present invention is described by way of example; the invention, whose breadth of application is evident from the entire description and from the claims, cannot be read as being confined to the embodiments specified in the examples.

Where reference is made below to ranges, numerical values, general formulae or classes of compound, they should be taken to encompass not only the corresponding ranges or groups of compounds that are explicitly mentioned, but also all subranges and numerical values and subgroups of compounds that may be obtained by extracting individual values (ranges) or compounds.

EXAMPLES

Materials Investigated

The sophorolipids looked at can be described by general formula 1 and/or 1a.

The crude product was prepared by means of fermentation with the yeast *Candida bombicola* on the basis of the substrates glucose, sunflower oil, rapeseed oil or olive oil (comprising primarily oleic acid as fatty acid fraction).

The growth medium contained the following constituents:
10 g/l glucose ((D)+glucose*$1H_2O$)
7.5 g/l YNB (Yeast Nitrogen Base)
2 g/l yeast extract 1.1 l of the medium were autoclaved in a fermenter with a capacity of 2 l and were seeded with an exponential-phase preculture from the same medium. The temperature was set to 30° C. The $pO_2$ was maintained at 30% relative saturation by admission of air via the stirrer speed, but the stirrer speed was never lower than 200 rpm. During the biomass formation phase, the pH fell to 3.5 and was maintained at this level by addition of NaOH. After the end of the biomass formation phase (consumption of the glucose present, marked by the rise in $pO_2$ or drop in $pCO_2$), the product formation phase was initiated by addition of 150 g of the corresponding oil, 200 ml of a 750 g/l glucose solution, and 10 ml of a 150 g/l yeast extract solution. The end of the product formation phase was marked by a renewed rise in $pO_2$. After the end of fermentation, the batch was autoclaved, with the crude product phase depositing as sediment. The crude product phase was washed with water and then with hexane. The product phase was subsequently extracted with ethyl acetate and then the solvent was removed under reduced pressure. This gave a largely water-free product, corresponding to the dry mass of the invention. Analysis by means of HPLC-MS and NMR showed that the product is composed largely of the diacetylated sophorolipid lactone form with glycosidically linked fatty acid (main constituents: sophorolipid lactone 65-80% by weight, fatty acid 1-16% by weight, glycerol 1-3% by weight).

TABLE 1

Overview of adjuvants investigated

| | |
|---|---|
| SLL | Sophorolipid = Dry mass (solid) |
| SLM | Sophorolipid methyl ester (solid) |
| SLS | Sophorolipid acid form (solid) |
| SLL-SLS | Sophorolipid lactone form in mixture with acid form, 50% in water |
| SLLF | Mixture of 30% SLL + 30% H2O + 20% nonanoic acid + 20% propylene glycol |

Standard adjuvant as comparative substance: BREAK-THRU® S 240 (alkoxylated trisiloxane from Evonik Goldschmidt GmbH)

Table 1 lists various derivatives of the fermentatively prepared sophorolipid SLL, which were tested later on in glasshouse trials.

The course of the derivatization steps was confirmed by NMR analysis.

SLL: The SLL corresponds to the dry mass of the fermentation process and forms a solid whose sophorolipid content is >80% by weight and which is present primarily in the lactone form of the sophorolipid (>90% by weight).

SLM: For the synthesis of the methyl ester and ethyl ester, SLL was dissolved in methanol or ethanol as solvent, and subjected to transesterification at a temperature of 60° C. for 3 hours by addition of $NaOCH_3$ or $NaOCH_2CH_3$ (pH=12). The solvent was then removed under reduced pressure. This gave a slightly viscous product which could be processed by freezing and subsequent grinding to a powder having a water solubility of >50% by weight (m/m).

SLS: A 60% by weight aqueous suspension of the sophorolipid SLL was admixed with 5% by weight of solid NaOH pellets. The mixture was then stirred at a temperature of 50° C. for 30 minutes in order to give, by hydrolysis, the deacetylated acid form of the sophorolipid. The batch was then adjusted to a pH of 3 by addition of HCl, and the product was extracted with ethyl acetate. Removal of the ethyl acetate gave a residue which can be ground to a powder and which has a water solubility of >50% by weight.

SLL-SLS: In this case, the procedure was as for SLS, but with the addition of only ¹⁄₁₀ of the NaOH, leading only to partial hydrolysis of the lactone form. This hybrid form was prepared with water to form a solution having a content of about 50% by weight.

Physical Properties:

a) Foam Behavior and Surface Tension:

For the parent structures, the foam behavior (by CIPAC Method MT 47) and the static surface tension were measured in 0.1% strength by weight aqueous solutions (on the sophorolipid preparation as present in adjuvant form). The surface tension of the 0.1% strength by weight solutions was measured by means of a bubble pressure tensiometer from SITA Messtechnik GmbH, instrument: Sita online t 60; SITA online Version 2.0. The bubble dwell time of the static surface tension is 30 ms. The measurement deviation is about 0.4%-1% of the reported mN/m figures. The measurements were carried out at an ambient temperature of 22° C. The figures shown are average values from three measurements.

According to CIPAC Definition, products which are "non-foaming" are products which generate only a foam of 5 ml in the volumetric flask with the method indicated. Low-foaming products are then defined here as those which exhibit values of ≤80 ml after 30 seconds.

b) Spreading Measurements:

The spreading properties were determined using a pipette and a biaxially oriented polypropylene film (FORCO OPPB AT-OPAL from 4P Folie Forchheim in Germany). One drop of an aqueous solution containing 0.1% by weight of the adjuvant, with a volume of 50 microliters, was applied to the film. The diameter of the drop was measured after one minute. If the drop did not spread circularly, the average value of the longest and shortest axes was calculated. The measurements were carried out in an acclimatized laboratory at 21.5° C. and 60% relative atmospheric humidity.

TABLE 2

Physical properties of inventive adjuvants/additives relative to the synthetic trisiloxane BREAK-THRU ® S240

| | BREAK-THRU ® S 240* | SLM | SLS | SLL-SLS 50% by weight in water | SLL |
|---|---|---|---|---|---|
| Static surface tension [mN/m] | 21.1 | 38.6 | 39.5 | 39.8 | 35.2 |
| Foam in ml (after 30 seconds) | 220 | 80 | 80 | 70 | 60 |
| Spreading [mm] | 70 | 8 | 9 | 8 | 10 |

* = Comparative substance - Organically modified trisiloxane

Evaluation of the Results from Table 2:

Surprisingly, only a low level of spreading is perceptible for the compositions of the invention, relative to the comparison substance BREAK-THRU® 5240. The formation of foam, however, is significantly reduced for the inventive formulations.

Performance Testing:

For the use of substances as formulating additives, only the physical/chemical compatibility with other formulating substances is important; however, the biological activity of a substance as adjuvant is always tested first of all on its own, in other words as a tank mix additive. As a basis for this invention, therefore, the confirmation of the biological activity is determined by means of tank mix trials in the glasshouse. Described below are glasshouse trials which serve for determining the improvement in biological action of pesticides with added adjuvants in crop protection. From among the large number of pesticides, the fungicides epoxiconazole and sulfur and the herbicide rimsulfuron were selected as examples here. In order to discover the synergism of the adjuvant, the trials below were conducted (see tables 5-7)

a) Adjuvant without addition of pesticide
 b) Pesticide use alone
 c) Pesticide plus adjuvant.

In order to be able to evaluate synergism, the results of c ought to be better than the sum of a and b; see also Colby formula.

In the trials set out in tables 3 and 4, only the influence of different adjuvants on the efficacy of the pesticides was tested.

Trial Setup for the Curative Trials:

In a glasshouse, the barley variety "Ingrid" (three plants per pot) was sown in "Frustosol" plant growth medium. Three weeks later, the leaves of the plants, measuring about 10-15 cm in length, were inoculated with fresh conidia of the mildew fungus *Blumeria graminis f.* sp. *hordei* (race A6) by means of an inoculating tower. Two days after this, they were sprayed with a spray solution containing the fungicide Opus® (125 g/l epoxiconazole) from BASF. The skilled person knows such trials as curative trials. The amount of spraying water corresponded to 250 l/ha. The dose of the fungicide was 10 ml/ha. The doses of the adjuvants varied between 50-125 ml (or g)/ha. In the case of water-diluted adjuvants/additives (such as the SLL-SLS), the dose is based on the active ingredient content. This quantity corresponded to about 0.0025%-0.5% by weight of the adjuvant/additive in the spray solution, which is comparable with standard adjuvants such as, for example, BREAK-THRU® S240.

Table 3 shows results of comparison between BREAK-THRU® 5240 and the sophorolipid SLL at the same concentrations. Here it is seen that the dose ought to be between 50-100 ml/ha, and that a concentration of the SLLs of greater than 50 g/ha does not produce any boost in action. Since no experience was available concerning an optimum dose of the sophorolipid, 75 ml/ha or 75 g a.i. (active ingredient)/ha were therefore taken as a basis for further tests for the sophorolipid preparations and derivatives thereof (see tables 5-7). In certain cases, the adjuvants/additives were also sprayed without fungicide, in order to examine whether the adjuvants/additives alone would display a biological action. When the spraying film had dried, leaf segments 8 cm long were cut from the treated plants and also from completely untreated plants, and for each variant 15 leaves were placed separately on benzimidazole agar in Petri dishes (0.5% agar, to which, after sterilization, 40 ppm of benzimidazole were added). After an incubation period of 14 days at room temperature, the infection of the leaves with mildew was investigated by estimating the proportion of infected leaf area. This trial setup is familiar to the skilled person.

The activity of the adjuvant alone, of the pesticide alone (i.e., of the fungicides or herbicides), and of the pesticide/adjuvant combination was calculated, in a manner known to the skilled person, in comparison to an untreated control sample, which was nevertheless inoculated with the mildew fungus, and expressed in % control of the disease.

Experimental Arrangement for the Protective Trials:

The plants (barley) were cultivated under glass in exactly the same way as in the curative trial. For the protective trials, however, the plants were sprayed at about three weeks old with spray solutions containing the active fungicidal ingredient sulfur (Microthiol WG 80% sulfur from Stähler), either alone or in combination with adjuvants/additives. Furthermore, in order to test for synergy, the adjuvant was applied in the spray solution alone, in other words without sulfur. The sulfur dose was 1000 ppm/l, while the adjuvants were used in different doses (for doses see results tables). The amount of spray solution was 250 l/ha, and so the adjuvant concentration in the spray solution was not more than 0.1%; the sulfur dose was 250 g/ha. After the spray solutions had dried on, leaf segments with a length of 8 cm were cut from the treated plants and also from entirely untreated plants, and for each variant 15 leaves were placed separately on benzimidazole agar in Petri dishes (0.5% agar, to which, after sterilization, 40 ppm of benzimidazole were added). The next day the plants were inoculated with fresh conidia of the mildew fungus *Blumeria graminis f.* sp. *hordei* (race A6) by means of an inoculation tower. An experimental arrangement of this kind is known to the skilled person as a protective trial, since the plants have been protected by fungicide prior to inoculation with the fungi. After an incubation period of 10 days at room temperature, the infection of the leaves with mildew was investigated by estimating the fraction of infected leaf area. This experimental setup is familiar to the skilled person.

The activity of the adjuvant alone, of the pesticide alone (i.e., of the fungicides or herbicides), and of the pesticide/adjuvant combination was calculated, in a manner known to the skilled person, in comparison to an untreated control sample, which was nevertheless inoculated with the mildew fungus, and expressed in % control of the disease.

Trials for Determining the Improvement in Biological Action of a Herbicide:

Under glass, blue grass (*Poa pratense*) was cultivated in pots. As soon as the plants had reached a height of about 5-7 cm, they were sprayed with spray solution containing the herbicide Cato® (DuPont, with 500 g/kg rimsulfuron). The amount of spraying water corresponded to 200 l/ha. This trial was also carried out in other versions, in which the spray solution contained various adjuvants as well as Cato®. For each element of the trial, three pots were treated identically, for reproducibility. The dose of the pesticide was 10 g/ha. As a commercial standard adjuvant, the trisiloxane BREAK-THRU® S240 from Evonik Goldschmidt GmbH was added at 50 and 100 ml/ha to the tank. The dose of the sophorolipids was between 50-250 ml or g/ha, meaning that the use concentration in the spray solution varied from 0.025% to 0.1% by weight. This was done intentionally in order to discover the optimum use concentration. Table 3 shows comparative results between the BREAK-THRU® 5240 and the sophorolipid SLL at identical concentrations. Here it is seen that the dose ought to be between 50-100 ml/ha and that a concentration of the SLLs of greater than 50 g/ha produces no boost in action. In the absence of experience concerning optimum dose of the sophorolipid, 75 ml/ha or 75 g a.i. (active ingredient)/ha was used as a basis for further tests with the sophorolipid preparations and derivatives thereof (see tables 5-7). Since the dose is always calculated on the amount of active ingredient, mostly 150 ml/ha is used for SLL-SLS, corresponding to 75 ml or g/ha of the SLL. Accordingly, the various sophorolipid preparation adjuvants are comparable with one another. In the case of the SLLF, this active ingredient concentration is achieved only when 250 ml/ha of the adjuvant is used. The effect of the treatments was scored 14, 20 or 30 days after application, by the methods known to the skilled person. Here, the damage to the plants as a result of the herbicide treatment is compared with untreated plants, and the activity of the spray treatment is expressed in relation to the untreated plants. The activity was determined on each of the three pots per trial. The average value was calculated and reported as percentage of efficacy in the results tables.

TABLE 3

Comparison of the boost in efficacy of different adjuvants on fungicides (14 days after application)

| Fungicide at 10 ml/ha | Adjuvant code | Adjuvant dose/ha | Efficacy (%) |
|---|---|---|---|
| Opus ® | none | 0 | 46% |
| Opus ® | BREAK-Thru ® S240 | 50 ml/ha | 91% |
| Opus ® | BREAK-Thru ® S240 | 100 ml/ha | 96% |
| Opus ® | SLL | 50 g/ha | 99% |
| Opus ® | SLL | 100 g/ha | 98% |

TABLE 4

Comparison of the boost in efficacy of different adjuvants on herbicides (30 days after application)

| Herbicide 10 g/ha | Wetting agent code | Wetting agent dose/ha | Efficacy (%) |
|---|---|---|---|
| Cato ® | none | none | 53% |
| Cato ® | BREAK-THRU ® S240 | 50 ml/ha | 70% |
| Cato ® | BREAK-THRU ® S240 | 100 ml/ha | 80% |
| Cato ® | SLL | 100 g/ha | 60% |
| Cato ® | SLL | 200 g/ha | 73% |

In tables 5-7, a dose is selected for the SLLF that makes it possible on the one hand to compare the adjuvant amount in relation to other sophorolipids (SLM or SLS)—this means the concentration of 125 ml/ha—but on the other hand an increased adjuvant concentration as well, in which case then, however, the amount of active sophorolipid ingredient at 75 g/ha a.i., is comparable. This means that 250 ml/ha of SLLF can be compared with 75 g/ha of SLM, or 150 ml/ha of the SLL-SLS, which in this case likewise contains 75 g/ha a.i.

TABLE 5

Comparison of different adjuvant derivatives and mixtures in curative fungicide trials (14 days after application)

| Fungicide | Adjuvant Code | Adjuvant dose/ha | Efficacy (%) |
|---|---|---|---|
| — | BREAK-THRU ® S240 | 50 ml/ha | 2% |
| — | SLL-SLS | 150 ml/ha = 75 g/ha a.i. of the SLL | 5% |
| — | SLLF | 250 ml/ha = 75 g/ha a.i. of the SLL | 6% |
| 10 ml/ha Opus ® | none | — | 38% |
| 10 ml/ha Opus ® | BREAK-THRU ® S240 | 50 ml/ha | 69% |
| 10 ml/ha Opus ® | SLM | 75 g/ha | 77% |
| 10 ml/ha Opus ® | SLM | 125 g/ha | 67% |
| 10 ml/ha Opus ® | SLS | 75 g/ha | 50% |
| 10 ml/ha Opus ® | SLS | 125 ml/ha | 63% |
| Opus ® | SLL-SLS | 150 ml/ha = 75 g/ha a.i. of the SLL | 44% |
| 10 ml/ha Opus ® | SLLF | 67.5 ml/ha = 18.7 g/ha a.i. of the SLL | 45% |
| 10 ml/ha Opus ® | SLLF | 125 ml/ha = 37.5 g/ha a.i. of the SLL | 58% |
| 10 ml/ha Opus ® | SLLF | 250 ml/ha = 75 g/ha a.i. of the SLL | 93% |

* a.i. = active ingredient

From table 5 it can be seen that a dose increase in the SLM is not accompanied by any enhanced activity. This was shown already in table 3. As a result, the dose of the BREAK-THRU® S240 (which in the case of this commercial product is prescribed by the approved dose in the label), of 50 ml/ha, can indeed be seen as comparable with that of the sophorolipids, of 75 g/ha a.i.

TABLE 6

Comparison of different adjuvant products and mixtures in protective fungicide trials (10 days after application)

| Fungicide | Adjuvant code | Adjuvant dose/ha | Efficacy (%) |
|---|---|---|---|
| None | BREAK-THRU ® S240 | 50 ml/ha | 8% |
| None | SLL-SLS | 150 ml/ha = 75 g/ha a.i. of the SLL | 9% |
| None | SLLF | 250 ml/ha = 75 g/ha a.i. of the SLL | 7% |
| Sulfur 250 g/ha | none | — | 46% |
| Sulfur 250 g/ha | BREAK-THRU ® S240 | 50 ml/ha | 68% |
| Sulfur 250 g/ha | SLM | 75 g/ha | 99% |
| Sulfur 250 g/ha | SLM | 125 g/ha | 90% |
| Sulfur 250 g/ha | SLS | 75 g/ha | 77% |
| Sulfur 250 g/ha | SLS | 125 ml/ha | 77% |
| Sulfur 250 g/ha | SLL-SLS | 150 ml/ha = 75 g/ha a.i. of the SLL | 85% |
| Sulfur 250 g/ha | SLL-SLS | 250 ml/ha = 125 g/ha a.i. of the SLL | 65% |
| Sulfur 250 g/ha | SLLF | 67.5 ml/ha = 18.7 g/ha a.i. of the SLL | 64% |
| Sulfur 250 g/ha | SLLF | 125 ml/ha = 37.5 g/ha a.i. of the SLL | 75% |
| Sulfur 250 g/ha | SLLF | 250 ml/ha = 75 g/ha a.i. of the SLL | 91% |

TABLE 7

Efficacy boost of different adjuvant products on
herbicides (20 days after application)

| Herbicide | Adjuvant code | Adjuvant dose/ha | Efficacy (%) |
|---|---|---|---|
| None | BREAK Thru ®S240 | 50 ml/ha | 0% |
| None | SLL-SLS | 150 ml/ha = 75 g/ha a.i. of the SLL | 0% |
| None | SLLF | 250 ml/ha = 75 g/ha a.i. of the SLL | 0% |
| Cato ® 10 g/ha | none | | 73% |
| Cato ® 10 g/ha | S240 | 50 ml/ha | 91% |
| Cato ® 10 g/ha | SLL-SLS | 150 ml/ha = 75 g/ha a.i. of the SLL | 86% |
| Cato ® 10 g/ha | SLLF | 250 ml/ha = 75 g/ha a.i. of the SLL | 88% |

Conclusions:

At selective dosages, the adjuvants/additives tested, especially sophorolipids, alone or in combination with nonanoic acid as co-surfactant, significantly improve the activity of pesticides, especially fungicides and herbicides, especially in comparison of their application alone and with addition of pesticide (synergism). Where the adjuvants/additives are tested alone—in other words, so to speak, as a biopesticide, as claimed in US 2005/0266036—(tables 5-7), at the selective dosages investigated they have no effect for the control of fungal diseases, or for the control or growth regulation of plants (see table 5: SLL-SLS or SLLF alone gave only an irrelevant 5% or 6% effect, which can come about as a result of fluctuations in experimental procedure). From this it can be concluded that the sophorolipids, where not used in combination with pesticides, exhibit no pesticidal effect. On the basis of the results listed, synergistic effects can be said to apply between sophorolipids and pesticides, with synergism being always present when the effect found for the mixture exceeds the sum of the individual effects. This is the case for the substances underpinning the invention. See table 6, for example. The sophorolipid SLL-SLS alone produced an activity of 9%, the pesticide alone one of 46%, whereas the activity of the combination, by virtue of the synergism, was 85%. Synergism is normally calculated according to the formula of Colby; see Colby S. R. 1967. Calculating synergistic and antagonistic responses of herbicide combinations, Weeds 15:20-22.

The Colby formula describes the anticipated effect: Anticipated efficacy (%)=x+y, or, when the sum of the efficacy percentages is >100%, according to the formula:

$$\text{Anticipated efficacy (\%)} = X + Y - \frac{X \cdot Y}{100}$$

where X is the efficacy (%) of the pesticide alone and Y is the efficacy (%) of the adjuvant alone.

The sophorolipids gave rise to efficacy boosts of pesticides, especially fungicides, which are comparable with commercial standards (such as BREAK-THRU® S240), or may be superior to the commercial standard, often even with the same dose (table 3). This is surprising, because the sophorolipids do not, like BREAK-THRU® 5240, exhibit a superspreading effect or greatly reduce the surface tension.

The application rate of the sophorolipids and/or derivatives thereof is 10-3000 ml or grams per hectare, preferably 50-700 ml or g/ha. This corresponds to the application rates of commercially available adjuvants in agriculture.

All derivatives of sophorolipids are active, though some more so than others. For instance, methyl esters of sophorolipids (SLM) are more active than NaOH hydrolyzed sophorolipids (SLS), both with contact pesticides (sulfur) and with pesticides having systemic activity (epoxiconazole). The activity of sophorolipids can be superproportionally boosted in certain cases, where, in binary systems, the efficacy of the pesticide cannot be sufficiently improved, by means of co-surfactants such as nonanoic acid, for example. Thus the sophorolipid (SLL-SLS) at 75 g a.i./ha active ingredient content develops a small boost in activity achieved together with the systemic fungicide Opus® (table 5) (44% fungicide plus adjuvant as against 38% fungicide alone), but together with nonanoic acid (SLLF), with the same amount of active sophorolipid ingredient present, i.e., with a dose of 250 ml/ha, produces a boost in efficacy to 93%. In a herbicide trial (table 7), the combination of herbicide and sophorolipid/nonanoic acid gave values comparable with those for the sophorolipid alone.

Since these sophorolipids and their derivatives do not possess any inherent fungicidal or herbicidal efficacy at the dosages used, there can be said to be synergies between biological surfactants for boosting the efficacy of pesticides, and the sophorolipids themselves can be termed adjuvant according to the PSD definition.

The invention claimed is:

1. A method for protecting a plant comprising:
providing an admixture of a pesticide and an adjuvant that is a lactone form of a sophorolipid in an aqueous solution; and applying said admixture to a plant, wherein said admixture of pesticide and adjuvant exhibits a synergistic effect in pesticidal activity, and wherein said lactone form of a sophorolipid is solubilized with clarity in said aqueous solution by a process comprising bringing a lactone form of a sophorolipid into said aqueous solution in the presence of a fatty acid, and adjusting the pH to 6-8.

2. The method as claimed in claim 1, wherein said adjuvant boosts the efficacy and/or enhances the activity of said pesticide, with the proviso that a dose range of the adjuvant lies between 10-3000 ml/ha.

3. The method as claimed in claim 1, wherein said admixture of the adjuvant and pesticide acts synergistically in a ratio of active pesticidal ingredient to adjuvant of 1:120 to 30:1.

4. The method as claimed in claim 1 wherein the pesticide is selected from the group consisting of herbicides, insecticides, growth regulators and/or fungicides or mixtures thereof, or plant strengtheners, micronutrients, and macronutrients.

5. The method as claimed in claim 4, wherein the pesticide is a contact fungicide, a systemic herbicide selected from the group of sulfonylureas, systemic fungicide selected from the class of triazoles, and mixtures of these and other pesticides.

6. The method as claimed in claim 1 wherein said adjuvant is present in an amount of 1% by weight to 99% by weight.

7. The method as claimed in claim 6, wherein the adjuvant is present in an amount of 1.5% by weight to 60% by weight.

8. The method as claimed in claim 1 wherein the plant is part of a crop.

9. The process as claimed in claim 1, wherein the fatty acid is selected from the group consisting of tallow, sunflower oil, rapeseed oil, safflower oil, soya bean oil, palm oil, palm kernel oil, coconut oil, olive oil, and short-chain to medium-chain carboxylic acids having an alkyl chain length of 6 to 22 carbon atoms.

10. The method as claimed in claim 1, wherein the fatty acid is selected from the group consisting of nonanoic acid (pelargonic acid), decanoic acid (capric acid), dodecanoic acid (lauric acid), tetradecanoic acid (myristic acid), hexadecanoic acid (palmitic acid), octadecanoic acid (stearic acid), octadecaenoic acid (oleic acid), and mixtures thereof.

11. The method as claimed in claim 1, wherein said lactone form of a sophorolipid is present as a mixture of said lactone form and an acid form, with an acid fraction of 10% to less than 60% by weight.

12. The method as claimed in claim 1, wherein said lactone form of a sophorolipid, in the absence of said fatty acid, and said fatty acid, in the absence of said lactone form of a sophorolipid, are not soluble with clarity in said aqueous solution.

13. A process for preparing a solubilized lactone form of a sophorolipid, said process comprising bringing a lactone form of a sophorolipid into solution in the presence of a fatty acid, and adjusting the pH to 6-8.

14. The process as claimed in claim 13, wherein the fatty acid, is selected from the group consisting of tallow, sunflower oil, rapeseed oil, safflower oil, soya bean oil, palm oil, palm kernel oil, coconut oil, olive oil, and short-chain to medium-chain carboxylic acids having an alkyl chain length of 6 to 22 carbon atoms.

* * * * *